United States Patent [19]
Ikeda et al.

[11] Patent Number: 5,489,577
[45] Date of Patent: Feb. 6, 1996

[54] SEMI-SOLID PHARMACEUTICAL AGENT AND PROCESS FOR PRODUCING THE SAME

[75] Inventors: Masao Ikeda; Tomoki Tatefuji; Hiroshi Yamauchi, all of Okayama, Japan

[73] Assignee: Kabushiki Kaisha Hayashibara Seibutsu Kagaku Kenkyujo, Okayama, Japan

[21] Appl. No.: 266,597

[22] Filed: Jun. 28, 1994

[30] Foreign Application Priority Data

Jun. 28, 1993 [JP] Japan ................... 5-178614

[51] Int. Cl.$^6$ ............... A61K 9/06; A61K 47/26
[52] U.S. Cl. ............ 514/53; 424/434; 424/435; 424/436; 424/DIG. 15; 514/2; 514/54; 514/61; 514/944; 514/967; 514/969; 514/970
[58] Field of Search .................... 424/434, 435, 424/436, DIG. 15; 514/53, 54, 61, 944, 967, 969, 970, 2

[56] References Cited

U.S. PATENT DOCUMENTS

| | | | |
|---|---|---|---|
| 4,226,848 | 10/1980 | Nagai et al. | 424/19 |
| 4,447,355 | 5/1984 | Sakamoto et al. | 260/112 B |
| 4,593,038 | 6/1986 | Burzynski | 514/328 |
| 4,650,665 | 3/1987 | Kronenthal et al. | 424/435 |
| 4,659,696 | 4/1987 | Hirai et al. | 514/15 |
| 4,670,419 | 6/1987 | Uda et al. | 514/16 |
| 4,851,220 | 7/1989 | Yim et al. | 424/85.7 |
| 5,011,824 | 4/1991 | Masada et al. | 514/13 |
| 5,028,416 | 7/1991 | Yano et al. | 424/59 |
| 5,194,261 | 3/1993 | Pichierri | 424/401 |
| 5,215,743 | 6/1993 | Singh et al. | 514/21 |
| 5,236,906 | 8/1993 | Yamamoto | 514/54 |
| 5,266,310 | 11/1993 | Mundorf et al. | 514/21 |
| 5,288,497 | 2/1994 | Stanley et al. | 424/440 |
| 5,318,780 | 6/1994 | Viegas et al. | 424/427 |
| 5,362,497 | 11/1994 | Yamada et al. | 424/449 |

Primary Examiner—Ronald W. Griffin
Attorney, Agent, or Firm—Browdy and Neimark

[57] ABSTRACT

Disclosed is a semi-solid pharmaceutical agent containing a stabilized proteinaceous bioactive substance prepared by successively mixing an oligosaccharide and an aqueous solution of a proteinaceous bioactive substance, and kneading the resultant solids with an oil or fat base. The pharmaceutical handles with ease because it is readily administered to the body through percutaneous and permucosal route which are safer and less in pain administration routes than other conventional administrations.

12 Claims, No Drawings

SEMI-SOLID PHARMACEUTICAL AGENT AND PROCESS FOR PRODUCING THE SAME

BACKGROUND OF THE INVENTION

1. Field of the Invention

The present invention relates to a semi-solid pharmaceutical agent and a process for producing the same, in particular, a stabilized semi-solid pharmaceutical agent with proteinaceous bioactive substances and a process for producing the same.

2. Description of the Prior Art

Semi-solid pharmaceutical agents containing chemicals as effective ingredient such as those in ointment or suppository form have been produced hitherto by simply kneading effective ingredients and bases. In case the effective ingredients are proteinaceous bioactive substances such as cytokines and hormones which are relatively labile, unlike chemicals, if one kneads them into semi-solid, then he or she will find that they have been already inactivated or they are still susceptible to inactivation and this renders such a semisolid infeasible unsuitable for actual uses.

Because of this, proteinaceous bioactive substances have been prepared into liquid forms where their activities were stably retained and then administered by injection through subcutaneous or intramuscular route in order for treatment of susceptable diseases, for example, immunopathies, viral disease, abnormalities in hormone secretion and malignant tumors.

While proteinaceous bioactive substances were found latter to be very efficacious in treatment of trauma in the skin and mucous membranes as well as of such a susceptible disease, therefore other administration methods such as percutaneous and permucosal injections, which are usually deemed to be safer and less painful, have been preferred. Thus development of semi-solid pharmaceutical agents using proteinaceous bioactive substances in stabilized form has been in great demand.

SUMMARY OF THE INVENTION

The present invention relates to a semi-solid pharmaceutical agent and a process for producing the same, in particular, a stabilized semi-solid pharmaceutical agent with proteinaceous bioactive substances and a process for producing the same.

To solve the aforementioned object, the present inventors energetically studied semi-solid pharmaceutical agents where saccharides were utilized. As the result, it was found first that after mixing aqueous solutions containing proteinaceous bioactive substances with a variety of saccharides and comparing the resultant solids for residual activity, the use of oligosaccharides, in particular, those exhibiting a strong hygroscopicity at a relative humidity of 75%, led to solids which were higher in residual activity ratio in comparison with monosaccharides, as well as that after subsequently mixing the resultant solids with a variety of base materials and investigating the resultant for stability of activities, semi-solid pharmaceutical agents with stabilized activity were obtained only when oil or fat bases were used. The present invention is based on this novel finding.

Thereafter the present inventors further investigated optimum combining ratios for these substances and materials, leading to the finding that semi-solids which contained for one part by weight of oligosaccharide about 0.02 or less parts by weight of proteinaceous bioactive substances and about 2 or more parts by weight of oil or fat bases were suitable as semi-solid pharmaceutical agents because they stably retained the activities of proteinaceous bioactive substances and exhibited appropriate extending and shape-retaining abilities. Thus the present inventors completed the invention.

DETAILED DESCRIPTION OF THE INVENTION

Oligosaccharides feasible in the invention are one or more di- through decasaccharides or their correspondent sugar alcohols which well retain the activities of proteinaceous bioactive substances so that one can produce stabilized semi-solid pharmaceutical agents: For example, disaccharides such as maltose, trehalose, lactose, sucrose and paratinose; oligosaccharide alcohols such as maltitol, lactitol and maltotriitol; maltooligosaccharides such as maltotriose, panose, maltotetraose and maltopentaose; oligosaccharides having the structure of sucrose within their molecules such as elurose, raffinose, meletitose, lactosylfructoside and maltosylfructoside; and other oligosaccharide mixtures such as "COUPLING SUGAR®", a glycosylsucrose commercialized by Hayashibara Co., Ltd.,Okayama, Japan, isomaltooligosaccharide, galactooligosaccharide, fructooligosaccharide are arbitrarily used.

In particular, oligosaccharides which notably well stabilize proteinaceous bioactive substances are anhydrous oligosaccharides which exhibit a strong hygroscopicity at a relative humidity of 75%. Such an oligosaccharide is feasible with those in substantially anhydrous form with the possible lowest moisture content, desirably, 3 w/w % or lower and a typical oligosaccharide is an anhydrous crystalline maltose product, "FINETOSE®", commercialized by Hayashibara Co., Ltd, Okayama, Japan. The moisture contents as referred to in the invention were those as determined by the Karl Fischer's method.

The wording "semi-solid pharmaceutical agent" as referred to in the invention means an agent in the form of an ointment, cream, cachou, suppository and the like other than an agent in the form of a powder and solid.

The wording "proteinaceous bioactive substance" as referred to in the invention means those including simple or complex proteins, more particularly, cytokines, for example, $\alpha$-, $\beta$- and $\gamma$-interferons, tumor necrosis factors $\alpha$ and $\beta$ (TNF-$\alpha$, TNF-$\beta$), epithelial cell growth factor (EGF), transfer factor, T cell growth factor (TCGF), and colony-stimulating factor (CSF), and proteinaceous hormone, for example, such as insulin, growth hormone, prolactin, chorionic gonadotropic hormone, erythropoietin, follicle-stimulating hormone, luteinizing hormone, adrenocorticotropic hormone, placental lactogen, thyroid-stimulating hormone and parathyroid-stimulating hormone which leave molecular weights up to 5,000–200,000.

Any proteinaceous bioactive substance is feasible in the invention regardless of preparation methods. Proteinaceous bioactive substances which are derived from body fluids, tissues and organs when they are inherently present, those from in vitro or in vivo cultures thereof and those from cultures of human cells, animal cells and microorganism wherein producibilities of such a substance has been introduced by conventional cell fusion and gene recombinant methods are all feasible in the invention.

In this invention, generally, proteinaceous bioactive substances are used in aqueous solution form at a concentration of about 5 w/v % or lower, desirably, $1 \times 10^{-5}$–3 w/v %.

Generally, one can produce solids such as powder, granule and block where the activities of the proteinaceous bioactive substances are stabilized by mixing one part by weight of solid oligosaccharide and about 0.4 or less parts by weight, desirably, 0.001–0.3 parts by weight of an aqueous solution of proteinaceous bioactive substance to a homogeneity as much as possible. If necessary, before completion of the step giving final products, a drying step using ventilation drying, vacuum drying and lyophilization and/or a sieving step is optionally provided.

To produce an objective semi-solid pharmaceutical agent with solids thus obtained, about 2 or more parts by weight to one part by weight of oligosaccharide, desirably, about 3–50 parts by weight of an oil or fat base, for example, white petrolatum, purified lanolin, cacao oil or "PHARMASOL®", commercialized by Nippon Oil and Fats Co., Ltd. Thus one can obtain stabilized semi-solid pharmaceutical agents according to the invention which contain one part by weight of oligosaccharide, about 0.02 or less parts by weight of proteinaceous bioactive substance and about 2 or more parts by weight of oil or fat base. If necessary, in the course of producing such a semi-solid pharmaceutical agent, conventional supplements, for example, stabilizer, absorption-promoting agent, bactericide, filler, taste-imparting agent, coloring agent and flavor-imparting agent can be used in combination so as to improve its efficacy and commercial value.

Semi-solid pharmaceutical agents thus obtained are favorably feasible, after cooling and shaping, in oral agents and a suppositories as well as in ointments in paste form because the use of "PHARMASOL®" or cacao oil stabilizes them at 30° C. or lower but brings them into melting form around 40° C. These semi-solids are suitable for pharmaceutical agents which are administered a through percutaneous or permucosal route. The amount of proteinaceous bioactive substance contained in such a semi-solid pharmaceutical agent can be arbitrarily chosen; for example, in the case of IFN-α, the present agent contains $10^2$–$10^8$ IU/g (The wording "IU" means international units.), in the case of IFN-γ, 10–$10^7$ IU/g and in the case of TNF-α, up to 10–$10^7$ IU/g.

The present semi-solid pharmaceutical agent is administered in ointment, cachou or suppository form, through the percutaneous and permucosal route, usually, 1–5 times a day in a dose up to 0.01–10g/adult, in order to treat susceptible diseases. These administration route and dose can be arbitrarily changed depending on the type and content of protein-aceous bioactive substances, as well as on the type of disease and patient's symptom.

The present invention will be explained in detail hereinafter in conjunction with several EXPERIMENTS:

EXPERIMENT 1

Influence of saccharides on the solidification of proteinaceous bioactive substance The stabilities of proteinaceous bioactive substances in solid compositions, obtained by mixing to homogeneity aqueous solutions containing proteinaceous bioactive substances with solid saccharides, were examined. In accordance with a conventional method, the proteinaceous bioactive substances used in the experiment were prepared by applying an interferon-α (IFN-α) preparation, an interferon-γ (IFN-γ) preparation or a tumor necrosis factor α (TNF-α) preparation, all of which are produced by Hayashibara Biochemical Laboratories, Inc., Okayama, Japan, and commercialized by Cosmo Bio Co., Ltd., Tokyo, Japan, to an antibody column fixed with each monoclonal antibody and after removing non-adsorbed fractions, adsorbed fractions were eluted from the column and concentrated by a membrane filter to obtain an about 0.01 w/v % aqueous solution.

The saccharides used in the experiment were monosaccharides such as hydrous crystalline glucose, anhydrous crystalline glucose, anhydrous crystalline fructose and anhydrous crystalline galactose; and oligosaccharides such as hydrous crystalline maltose, anhydrous crystalline maltose, anhydrous crystalline maltitol, hydrous crystalline trehalose, anhydrous crystalline trehalose, anhydrous crystalline neotrehalose, hydrous crystalline lactose, anhydrous crystalline lactose, anhydrous crystalline sucrose, anhydrous crystalline panose, anhydrous crystalline lactosylglucoside, anhydrous amorphous lactosylfructoside (alias lactosucrose), anhydrous amorphous maltotetraose and anhydrous amorphous glycosylsucrose (COUPLING SUGAR®).

To 50 parts by weight of each oligosaccharide was added one part by weight of an aqueous solution containing one of the proteinaceous bioactive substances prepared by the above method, and mixed as homogeneously as possible while spraying the solution onto the oligosaccharide. The resultant mixture was allowed to stand at 30° C. for 18 hours and pulverized to obtain a powder containing a proteinaceous bioactive substance. After one-month standing of the resultant powder under drying conditions at 40° C., the residual activity of the proteinaceous bioactive substance was determined. The percentage of the residual activity to the initial activity in the starting aqueous solution was considered as the percentage of the residual activity (%), i.e., the index of the stability of the proteinaceous bioactive substance in the powder. While each saccharide used as a material was determined the level of its hygroscopicity by allowing it to stand at a relative humidity of 75% and a temperature of 30° C. for 6 days, and determining the final weight. The difference between the final weight and the starting weight was determined and considered as the weight increased by moisture absorption, and the percentage of the increased weight against the starting weight was considered as the ratio of moisture absorption (%), i.e., the index of the level of hygroscopicity. The results were as shown in Table 1.

TABLE 1

| Saccharide | Percentage of hygroscopicity (%) | IFN-α | IFN-γ | TNF-α | Judgement |
| --- | --- | --- | --- | --- | --- |
| (A)Hydrous crystalline | Less than 1.0 | 15.1 | 0 | 0 | Impassable |

TABLE 1-continued

| Saccharide | Percentage of hygroscopicity (%) | IFN-α | IFN-γ | TNF-α | Judgement |
|---|---|---|---|---|---|
| glucose | | | | | |
| (A)Anhydrous crystalline glucose | Less than 1.0 | 25.7 | 0 | 0 | Impassable |
| (A)Anhydrous crystalline fructose | Less than 1.0 | 13.6 | 0 | 0 | Impassable |
| (A)Hydrous crystalline | Less than 1.0 | 12.4 | 0 | 0 | Impassable |
| (B)Hydrous crystalline maltose | Less than 1.0 | 47.2 | 22.5 | 9.2 | Passable |
| (B)Anhydrous crystalline maltose | 5.9 | 98.7 | 56.4 | 61.1 | Excellent |
| (B)Anhydrous crystalline maltitol | Less than 1.0 | 49.2 | 24.8 | 10.6 | Passable |
| (B)Hydrous crystalline trehalose | Less than 1.0 | 44.9 | 31.8 | 8.0 | Passable |
| (B)Anhydrous crystalline trehalose | 9.8 | 86.1 | 52.6 | 57.4 | Excellent |
| (B)Anhydrous crystalline neotrehalose | Less than 1.0 | 35.4 | 14.0 | 7.3 | Passable |
| (B)Hydrous crystalline lactose | Less than 1.0 | 33.1 | 2.6 | 5.4 | Passable |
| (B)Anhydrous crystalline lactose | Less than 1.0 | 45.4 | 9.3 | 9.1 | Passable |
| (B)Anhydrous crystalline sucrose | Less than 1.0 | 33.5 | 20.8 | 8.0 | Passable |
| (B)Anhydrous crystalline penose | Less than 1.0 | 36.2 | 14.4 | 36.5 | Passable |
| (B)Anhydrous crystalline lactosylglucoside | Less than 1.0 | 32.3 | 28.6 | 29.4 | Passable |
| (B)Anhydrous amorphous lactosylfructoside | 21.4 | 98.8 | 75.6 | 70.1 | Excellent |
| (B)Anhydrous amorphous maltotetraose | 20.3 | 66.2 | 47.1 | 50.3 | Excellent |
| (B)Anhydrous amorphous glycosylsucrose | 22.6 | 80.1 | 65.9 | 55.2 | Excellent |

Note: (A) means monosaccharide, and (B) means oligosaccharide.

These data confirmed that the solidification of a proteinaceous bioactive substance under the coexistence of an oligosaccharide is suitable for the stabilizing the proteinaceous bioactive substance. It is found that oligosaccharides which exert high hygroscopicity of 5% or higher at a relative humidity of 75% and 30° C. for 6 days are satisfactorily used, more particularly, anhydrous oligosaccharides such as anhydrous crystalline maltose, anhydrous crystalline trehalose, anhydrous amorphous lactosylfructoside and anhydrous amorphous glycosylsucrose are suitably used.

EXPERIMENT 2

Influence of bases on semi-solidification of proteinaceous bioactive substances solidified by oligosaccharides A powdery IFN-α stabilized with anhydrous crystalline maltose, a powdery IFN-γ stabilized with anhydrous amorphous lactosylfructoside or a powdery TNF-α stabilized with anhydrous amorphous lactosylfructoside, prepared by the method in EXPERIMENT 1, was kneaded with a semi-solid base in the usual manner, and the stability of the activity of the proteinaceous bioactive substances in the resultant semi-solid bases were compared.

One part by weight of a powdery proteinaceous bioactive substance was kneaded with 9 parts by weight of a water-soluble base, an emulsion base or an oil or fat base, and allowed to stand under a relative humidity of 75% and a temperature of 30° C. After one-month standing, the residual activity of the proteinaceous bioactive substance was determined, followed by calculating the percentage of the residual activity against the starting activity, i.e., the percentage of the residual activity (%) or the index of the stabilization of a proteinaceous bioactive substance in semi-solid pharmaceutical. Furthermore, those prepared with oil or fat bases were heated in phosphate buffer at 40° C. for 30 minutes to dissolve and isolate the oil or fat bases. The activity of the proteinaceous bioactive substance in the resultant aqueous solution was determined in usual manner. The results were as shown in Table 2.

TABLE 2

| Solid Base | coexistence of IFN-α and anhydrous crystalline maltose | coexistence of IFN-γ and anhydrous crystalline lactosylfructoside | coexistence of TNF-α and anhydrous crystalline lactosylfructoside | Judgement |
|---|---|---|---|---|
| (A)Macrogol Ointment | 0 | 0 | 0 | Impassable |
| (A)HIVIS | 0 | 0 | 0 | Impassable |

TABLE 2-continued

| Solid Base | coexistence of IFN-α and anhydrous crystalline maltose | coexistence of IFN-γ and anhydrous crystalline lactosylfructoside | coexistence of TNF-α and anhydrous crystalline lactosylfructoside | Judgement |
|---|---|---|---|---|
| WAKO GEL® |  |  |  |  |
| (B)Vanishing Cream | 0 | 0 | 0 | Impassable |
| (B)Cold Cream | 0 | 0 | 0 | Impassable |
| (C)White Petrolatum | 100 | 100 | 100 | Passable |
| (C)PHARMASOL® | 100 | 100 | 100 | Passable |

Note: Values in the Table 2 mean residual percentages (%) of residual activity. (A) means a water-soluble base, (B) means an emulsion base and (C) means an oil and fat base.

As is obvious from Table 2, it was found that the powders containing proteinaceous bioactive substances which were solidified by oligosaccharides can be made into semi-solid pharmaceuticals containing stabilized proteinaceous bioactive substances, only by mixing the proteinaceous substances with oil or fat bases.

EXPERIMENT 3

Influence of the mixing ratio of powdery proteinaceous bioactive substance and oil or fat base on the formation of semi-solid pharmaceutical One part by weight of a powdery IFN-α stabilized with anhydrous crystalline maltose, obtained by the method in EXPERIMENT 1, was kneaded with 0.1, 0.5, 1, 2, 5, 10 or 20 parts by weight of white petrolatum or "PHARMASOL®", and the resultant mixture was allowed to stand at about 25° C. for one hour, followed by the observation of the form of the resultant product. After 6-months standing of the product under a relative humidity of 75% and a temperature of 30° C., the residual activity of the IFN-α was determined and the percentage of the residual activity against the starting activity was calculated, as the percentage of the residual activity (%), i.e., the index of the stabilization of proteinaceous bioactive substances in the products. For the sake of the comparison, powdery proteinaceous bioactive substances were allowed to stand under the same condition for 6-months, followed by calculating the percentage of (%) of the residual activity. The results were as shown in Table 3.

TABLE 3

| Part by weight of an oil and fat base against one part by weight of a solid | | Form | Residual activity (%) | Judgement |
|---|---|---|---|---|
|  | 0 | Powdery | 0 | Control |
| (A) | 0.1 | Nearly powdery | 0 | Impassable |
| (A) | 0.5 | Gel | 15.8 | Impassable |
| (A) | 1.0 | Pasty | 64.6 | Passable |
| (A) | 2.0 | Pasty | 100 | Excellent |
| (A) | 5.0 | Pasty | 100 | Excellent |
| (A) | 10.0 | Pasty | 100 | Excellent |
| (A) | 20.0 | Pasty | 100 | Excellent |
| (B) | 0.1 | Nearly powdery | 0 | Impassable |
| (B) | 0.5 | Gel | 20.4 | Impassable |
| (B) | 1.0 | Solid | 73.6 | Passable |
| (B) | 2.0 | Solid | 100 | Excellent |
| (B) | 5.0 | Solid | 100 | Excellent |
| (B) | 10.0 | Solid | 100 | Excellent |
| (B) | 20.0 | Solid | 100 | Excellent |

Note:(A) means white petrolatum and (B) means PHARMASOL®.

As is obvious from Table 3, it was found that the suitable mixing ratio of an oil or fat base to one part by weight of a solid containing proteinaceous bioactive substance is about 2 parts by weight, which keeps the resultant product in a desirable form and in a high residual activity.

EXPERIMENT 4

Influence of production condition on the semi-solid pharmaceutical

The influence of materials to be mixed and mixing procedure on the stabilization of proteinaceous bioactive substances in the resultant semi-solid pharmaceuticals was examined.

Sample A was a product which was produced by the representative preparation of the invention, which was prepared by the method in EXPERIMENT 1 by successively mixing homogeneously one part by weight of an aqueous solution containing 0.01 w/v % of IFN-α with 50 parts of weight of anhydrous crystalline maltose into a solid which was then kneaded with white petrolatum by the method in EXPERIMENT 2. The following each sample as a control was prepared by using the same mixing ratio (part by weight) as in sample A. A semi-solid pharmaceutical, sample B, was obtained by successively kneading anhydrous crystalline maltose with white petrolatum and kneading the resultant mixture with an aqueous solution containing IFN-α as homogeneously as possible.

A semi-solid pharmaceutical, sample C, was obtained by successively kneading anhydrous crystalline maltose with white petrolatum and kneading as homogeneously as possible the resultant substance with a lyophilized product prepared from an aqueous solution containing IFN-α.

A semi-solid pharmaceutical, sample D, was obtained by successively kneading white petrolatum with an aqueous solution containing IFN-α as homogeneously as possible.

A semi-solid pharmaceutical, sample E, was obtained by successively kneading white petrolatum with a lyophilized product prepared from an aqueous solution containing IFN-α.

These samples were allowed to stand under a relative humidity of 75% and a temperature of 40° C. After one-month standing, the residual activity of IFN-α in each sample was determined and the percentage (%) of the residual activity against the activity in the material aqueous solution was determined as the percentage (%) of the residual activity, i.e., the index of the stabilization of the proteinaceous bioactive substance in the semi-solid pharmaceutical. The results were as shown in Table 4.

TABLE 4

| Sample | Production condition | Residual activity (%) | Judgement |
|---|---|---|---|
| A | (Anhydrous crystalline maltose + Aqueous IFN-α solution) + White petrolatum | 100 | Present invention |
| B | (Anhydrous crystalline maltose + White petrolatum) + Aqueous IFN-α solution | 4.7 | Control |
| C | (Anhydrous crystalline maltose + White petrolatum) + Dried IFN-α | 25.1 | Control |
| D | White petrolatum + Aqueous IFN-α solution | 2.7 | Control |
| E | White petrolatum + Dried IFN-α | 38.4 | Control |

As is obvious from Table 4, it was found that the semi-solid pharmaceuticals containing stabilized proteinaceous bioactive substances were obtained by successively mixing aqueous solutions containing proteinaceous bioactive substances with oligosaccharides and kneading the resultant mixtures with oil or fat bases. It was also found that it is impossible to achieve the present object when oligosaccharides are not used in the materials for the present semi-solid pharmaceutical or when their mixing order is changed.

Several examples of the present invention will hereinafter be described, but do not limit the scope of the present invention:

EXAMPLE 1

Ointment containing IFN-α

Newborn hamsters were injected with antiserum prepared in conventional manner to weaken their immunoreaction, implanted subcutaneously with BALL-1 cells and fed in the usual manner for 3 weeks. The tumor masses, formed subcutaneously in the body of the hamsters, were extracted, minced and disaggregated in saline. The cells thus obtained were washed with serum-free RPMI 1640 medium (pH 7.2), suspended in a fresh preparation of the same medium to give a cell density of about $2 \times 10^6$ cells/ml, kept at 35° C. The cell suspension was mixed with 200 μ/ml of a partially purified IFN-α, kept at this temperature for 2 hours, mixed with about 300 hemagglutination titer/ml of Sendai virus at this temperature, and incubated for 20 hours to induce IFN-a. The resultant culture was centrifuged to remove insoluble substances at about 1,000×g and about 4° C., and the supernatant was concentrated with a membrane filter, and the concentrate was a column of immobilizled anti-IFN-α antibody in conventional manner, followed by removing a non-adsorbed fraction. Thereafter, an adsorbed fraction was eluted from the column and concentrated with a membrane filter to obtain an about 0.5 w/v % liquid preparation containing human IFN-α having a specific activity of about $2 \times 10^8$ IU/mg protein.

One part by weight of a liquid preparation obtained by the method in EXAMPLE 1 was mixed as homogeneously as possible with 49 parts by weight of anhydrous crystalline maltose to obtain a solid preparation containing IFN-α which was then kneaded with 3-times by volume of white petrolatum to obtain an ointment containing IFN-α. The product had about $5 \times 10^6$ IU/g of IFN-α. The product, an ointment containing a stabilized IFN-a, can be advantageously used for treating IFN-α susceptible diseases such as an infectious disease of herpes virus, a cutaneous cancer, a rhinitis and a conjunctivitis by applying it to the skin or the mucous membrane.

EXAMPLE 2

Suppository containing IFN-α

A solid preparation containing human IFN-α, obtained by the method in EXAMPLE 1, was mixed with 9-times by volume of "PHARMASOL®" which had been dissolved by heating at 40° C., and the mixture was poured into a mold and cooled to obtain a suppository containing IFN-α. The product had about $2 \times 10^6$ IU/g of IFN-α. The product, a suppository containing a stabilized IFN-α, can be advantageously used for treating susceptible diseases of IFN-α such as an infectious disease of herpes virus, a hepatitis and a malignant tumor by administering it into the rectum and the vagina.

EXAMPLE 3

Ointment containing IFN-γ

According to the method in EXPERIMENT 1, a commercially available human IFN-γ preparation was applied to an anti-IFN-γ antibody column in conventional manner. After the non-adsorbed fraction was removed, an adsorbed fraction was eluted, and concentrated with a membrane filter to obtain an about 0.5 w/v % solution containing human IFN-γ having a specific activity of about $2 \times 10^7$ IU/mg protein.

One part by weight of the solution and 29 parts by weight of anhydrous crystalline trehalose were mixed as homogeneously as possible into a solid product containing IFN-γ, which was then kneaded with 4-times by volume of purified lanolin to obtain an ointment containing IFN-γ.

The product had about $3 \times 10^5$ IU/g of IFN-γ. The product, an ointment containing a stabilized IFN-γ, can be advantageously used for treating IFN-γ susceptible diseases such as an infectious disease of virus, a hepatitis , an articular rheumatism, a rhitis and a conjunctivitis by applying it to the skin and the mucous membrane similarly as the product of EXAMPLE 1.

EXAMPLE 4

Suppository containing TNF-α

A non-adsorbed fraction of anti-IFN-α antibody, prepared by the method in EXAMPLE 1, was eluted and concentrated with a membrane filter to obtain an about 0.5 w/v % concentrated solution containing human TNF-α having a specific activity of about $2 \times 10^7$ IU/mg protein.

One part by weight of the solution and 49 parts by weight of anhydrous amorphous lactosylfructoside were mixed as homogeneously as possible into a solid product containing TNF-α which was then kneaded with 3-times by volume of "PHARMASOL®" to obtain a suppository containing TNF-α.

The product had about $3\times10^5$ IU/g of TNF-α. The product, a suppository containing a stabilized TNF-α, can be advantageously used for treating TNF-α susceptible diseases such as a malignant tumor, an infectious disease of virus and an immunopathy by administering it into the rectum and the vagina.

EXAMPLE 5

Cachou containing cytokine 0.5 parts by weight of a solution containing human IFN-α prepared by the method in EXAMPLE 1, 0.25 parts by weight of a solution containing human IFN-γ prepared by the method in EXAMPLE 3, 0.25 parts by weight of a solution containing human TNF-α prepared by the method in EXAMPLE 4 and 9 parts by weight of an aqueous solution containing about 0.5 w/v % bovine serum albumin were mixed, and the mixture and 490 parts by weight of anhydrous crystalline maltose were mixed as homogeneously as possible into a solid product containing cytokine. The solid was mixed with 4-times by volume of cocoa butter previously dissolved by heating, adequate amounts of a coloring agent and a flavor-imparting agent, and the mixture was poured into a mold and cooled to obtain a cachou containing cytokine.

The product, having about $1\times10^5$ IU/g of IFN-α, about $3\times10^3$ IU/g of IFN-γ and about $3\times10^3$ IU/g of TNF-α, is a cachou containing 3 types of stabilized cytokines. Since the efficacy of IFN-α, IFN-γ and TNF-α is exerted synergistically, it is much more effective for treating IFN-α, IFN-γ and TNF-α susceptible diseases such as an immunopathy, an infectious disease of virus and a malignant tumor by administering it to the mouth.

EXAMPLE 6

Suppository containing cytokine

A mixture solution containing cytokine, which was prepared by the method in EXAMPLE 5, and 490 parts by weight of anhydrous crystalline trehalose were mixed as homogeneously as possible to obtain a solid containing cytokine which was then poured into a mold and cooled to obtain a suppository containing cytokine.

The product, having about $4\times10^4$ IU/g of IFN-α, about $1\times10^3$ IU/g of IFN-γ and about $1\times10^3$ IU/g of TNF-α, is a suppository containing 3 types of stabilized cytokines. Since, the efficacy of IFN-α, IFN-γ and TNF-α is exerted synergistically, it is much more effective for treating IFN-α, IFN-γ and TNF-α susceptible diseases such as an immunopathy, an infectious disease of virus and a malignant tumor by administering it into the rectum and the vagina.

EXAMPLE 7

Ointment containing EGF 0.0001 part by weight of a commercially available recombinant human EGF was dissolved in one part by weight of phosphate-buffered saline (pH 7.2), and the resultant solution was mixed with 49 parts by weight of anhydrous crystalline maltose as homogeneously as possible to obtain a solid. The resultant solid was kneaded with 9-times by volume of white petrolatum to obtain an ointment containing EGF.

The product had about 0.2 µg/g of active EGF. The product, an ointment containing a stabilized EGF, can be advantageously used for treating EGF susceptible diseases such as a trauma, an incision, an abrasion and a burn by applying it to the skin or the mucous membrane to effectively treat them.

EXAMPLE 8

Oral agent containing insulin 0.1 part by weight of a commercially available recombinant human insulin having a specific activity of about 24 IU/mg protein was dissolved in one part by weight of phosphate-buffered saline (pH 7.0), and the resultant solution was mixed with 49 parts by weight of anhydrous crystalline maltose as homogeneously as possible into a solid. The resultant solid was kneaded with 19-times by volume of cocoa butter, which had been previously dissolved by heating, and an adequate amount of a flavor-imparting agent, and the mixture was poured into a mold and cooled to obtain an oral agent containing insulin.

The product had about 21 IU/g of insulin. The product, an oral agent containing a stabilized insulin, can be advantageously used for keeping the blood sugar level of diabetics within a normal level by administering them about 2–6 IU/day of insulin.

EXAMPLE 9

Suppository containing erythropoietin 0.01 part by weight of a commercially available human erythropoietin derived from urine having a specific activity of about $1\times10^5$ IU/mg protein was dissolved in phosphate-buffered saline (pH 7.2), and the resultant solution was mixed with 49 parts by weight of anhydrous crystalline trehalose as homogeneously as possible to obtain a solid. The resultant solid was mixed with 39-times by volume of "PHARMASOL®" which had been previously dissolved by heating, and the mixture was poured into a mold and cooled to obtain a suppository containing erythropoietin.

The product has about 500 IU/g of erythropoietin. The product, a suppository containing a stabilized erythropoietin, can be advantageously used for maintaining the number of erythocytes for anemic patients by administering to them about 1,000–6,000 IU/day of erythropoietin.

[Effect of the invention]

As described above, the present invention established semi-solid pharmaceuticals containing stabilized proteinaceous bioactive substances in the form of an ointment and a suppository. The preparations comprise mixing solutions containing proteinaceous bioactive substances with oligosaccharides to obtain solid products, and kneading the resultant solid products with oil or fat bases.

Proteinaceous bioactive substances contained in the semi-solid pharmaceuticals are effective for treating susceptible diseases, and the oil or fat bases protect the skin and the mucous membrane. The oligosaccharides in the semi-solid pharmaceuticals attain more satisfactory therapeutic efficacy to supplement energy to cells and cellular tissues. The present semi-solid pharmaceutical handles easily because it is readily administered to the body by percutaneous and permucosal routes which are safer and less painful administration routes than conventional administration routes.

What is claimed is:

1. A semi-solid pharmaceutical composition containing a stabilized proteinaceous bioactive substance, which comprises one part by weight of at least one anhydrous oligosaccharide, selected from the group consisting of di- through decasaccharides, not more than 0.02 parts by weight of a proteinaceous bioactive substance, and at least 2 parts by weight of an oil or fat base, wherein said proteinaceous bioactive substance is stabilized by said anhydrous oligosaccharide and said oil or fat base.

2. The semi-solid pharmaceutical composition in accordance with claim 1, wherein said proteinaceous bioactive substance is a member selected from the group consisting of cytokines, hormones, and mixtures thereof.

3. The semi-solid pharmaceutical agent in accordance with claim 1, wherein said oligosaccharide is one which exhibits a strong hygroscopicity at a relative humidity of 75%.

4. The semi-solid pharmaceutical agent in accordance with claim 1, wherein said oil or fat base is a member selected from the group consisting of white petrolatum, lanolin, glycerides, and mixtures thereof.

5. The semi-solid pharmaceutical agent in accordance with claim 1, which is in the form of an ointment, a cachou or a suppository.

6. A process for preparing a semi-solid pharmaceutical agent, which comprises mixing an anhydrous oligosaccharide and a solution of a proteinaceous bioactive substance, and kneading the resultant solid with an oil or fat base, wherein not more than 0.4 parts by weight of said aqueous solution and at least 2 parts by weight of said oil or fat base are incorporated into one part by weight of said anhydrous oligosaccharide, said anhydrous oligosaccharide being selected from the group consisting of di- through decasaccharides and mixtures thereof.

7. The process in accordance with claim 6, wherein said solution is an aqueous solution.

8. The process in accordance with claim 6, wherein said proteinaceous bioactive substance is a member selected from the group consisting of cytokines, hormones and mixtures thereof.

9. The process in accordance with claim 6, wherein said solution contains at most about 5 w/v % of said proteinaceous bioactive substance.

10. The process in accordance with claim 8, wherein said oligosaccharide is one which exhibits a strong hygroscopicity at a relative humidity of 75%.

11. The process in accordance with claim 6, wherein said oil or fat base is a member selected from the group consisting of white petrolatum, lanolin, glycerides, and mixtures thereof.

12. The process in accordance with claim 6, wherein said semi-solid pharmaceutical agent is in the form of an ointment, a cachou or a suppository.

* * * * *